(12) United States Patent
Blevis et al.

(10) Patent No.: US 8,384,015 B2
(45) Date of Patent: Feb. 26, 2013

(54) CALIBRATION SOURCE AND METHODS FOR CALIBRATING A NUCLEAR MEDICINE IMAGING SYSTEM

(75) Inventors: Ira Blevis, Zichron Yaakov (IL); Yaron Hefetz, Kibbutz alonim (IL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/646,922

(22) Filed: Dec. 23, 2009

(65) Prior Publication Data

US 2011/0147574 A1 Jun. 23, 2011

(51) Int. Cl.
*G01D 18/00* (2006.01)
(52) U.S. Cl. .............. 250/252.1; 250/493.1; 250/363.09
(58) Field of Classification Search ............... 250/252.1, 250/493.1, 363.09
See application file for complete search history.

(56) References Cited

U.S. PATENT DOCUMENTS

| | | | |
|---|---|---|---|
| 3,591,806 A | 7/1971 | Brill et al. | |
| 5,561,698 A | 10/1996 | Mick et al. | |
| 5,677,536 A | 10/1997 | Vickers | |
| 5,986,266 A | 11/1999 | Andreaco et al. | |
| 6,624,422 B2 | 9/2003 | Williams et al. | |
| 6,635,893 B2 * | 10/2003 | O'Kane et al. | 250/506.1 |
| 6,858,850 B2 | 2/2005 | Williams et al. | |
| 7,385,184 B2 * | 6/2008 | Yeh et al. | 250/252.1 |
| 7,449,680 B2 | 11/2008 | Wang et al. | |
| 7,497,621 B2 | 3/2009 | Yatesenko et al. | |
| 7,573,025 B2 | 8/2009 | Yokoi et al. | |
| 2005/0072914 A1 | 4/2005 | Chapman | |
| 2006/0180767 A1 * | 8/2006 | Ramsden | 250/369 |
| 2006/0214097 A1 | 9/2006 | Wang et al. | |
| 2007/0081940 A1 * | 4/2007 | O'Foghludha | 424/1.11 |
| 2007/0145257 A1 * | 6/2007 | Petrillo et al. | 250/252.1 |
| 2007/0252079 A1 | 11/2007 | Wang et al. | |
| 2008/0093544 A1 * | 4/2008 | Wang et al. | 250/252.1 |
| 2011/0174963 A1 * | 7/2011 | Botterweck | 250/252.1 |

FOREIGN PATENT DOCUMENTS

| | | |
|---|---|---|
| EP | 2347282 A2 | 7/2011 |
| WO | WO 2009/071619 A1 | 6/2009 |

OTHER PUBLICATIONS

Search Report from GB Intellectual Property Office, Application No. GB1021346.0, Date of Search: Apr. 18, 2011, (2) pgs.
IEEE Nuclear Science Symposium (2003), vol. 3, Barber et al., "Simultaneous dual-isotope SPECT with a single CdZnTe detector", (2) pgs.
IEEE Nuclear Science Symposium and Medical Imaging Conference (2009), Mikeli et al., "Collimator study of a [gamma]-camera system using GATE", pp. 3931-3935.
http://www.biodex.com/radio/sources/sources_830.htm.
GB Search Report, Application No. GB1021346.0, Date of Search: Nov. 4, 2011, (2 pgs.).

* cited by examiner

*Primary Examiner* — Christine Sung
(74) *Attorney, Agent, or Firm* — The Small Patent Law Group; Dean D. Small (57) ABSTRACT

Systems and methods for calibrating a nuclear medicine (NM) imaging system are provided that include an NM calibration source. The NM calibration source includes an isotope source having an energy spectrum with at least one energy peak and a fluorescence layer adjacent the isotope source creating at least one additional energy peak in the energy spectrum.

34 Claims, 7 Drawing Sheets

CALIBRATION SOURCE AND METHODS FOR CALIBRATING A NUCLEAR MEDICINE IMAGING SYSTEM

BACKGROUND OF THE INVENTION

The subject matter disclosed herein relates generally to nuclear medicine (NM) imaging systems, and more particularly to systems and methods for calibrating the detectors of NM imaging systems.

NM imaging systems, for example Single Photon Emission Computed Tomography (SPECT) and Positron Emission Tomography (PET) imaging systems, use one or more image detectors to acquire image data, such as gamma ray or photon image data. The image detectors may be gamma cameras that acquire two-dimensional views of three-dimensional distributions of emitted radionuclides (from an injected radioisotope) from a patient being imaged.

In single photon imaging systems, such a planar or SPECT imaging systems, collimators may be placed in front of a scintillation crystal or solid state detector to focus the field of view (FOV) of the detectors. The collimators allow gamma rays aligned with the holes of the collimators to pass through to the detector. These detectors need to be calibrated, including during manufacture and periodically after installation to ensure proper imaging operation. For example, the detectors are calibrated to provide a uniform energy and sensitivity response across the detector units or output channels.

Calibration of these collimated detectors is performed using a calibration emission source that exposes the detectors, and more particularly the entire detector or array of detectors, to radioactive emissions. Accordingly, in pixelated detectors, each pixel is exposed to a statistically relevant number of photons. In some collimated detector systems, calibration with multiple isotopes (having different energy peaks) is not practical after the system is assembled. Accordingly, in collimated detectors, the calibration is performed on the detectors having the collimators removed and using a jig or guide. This enables a two point energy calibration (gain and offset), wherein the calibration uses at least two isotope sources with two different peaks for calibration. A point source, however, cannot be used on the assembled system as the collimators at least partially obscure some parts of the detector. Thus, because the collimators need to be removed for calibration, detector calibration can easily be performed at the factory, but not after installation, for example, at a medical site, such as if parts of the detector are replaced.

Moreover, the presence of the collimators, such as in the assembled imaging systems, allows the use of flood sources only to expose or illuminate the entire detector, namely all the pixels, for calibration. Flood sources are difficult to handle and use. Additionally, the flood source can cause problems and have safety issues due to the significant radiation emitted by these flood sources. Flood sources are also more expensive than point sources and generally are available for only a limited number of isotopes. Shielding a large flood source is heavy and cumbersome. Generally, a hospital or a field serviceman may have one flood source for performing quality control and field calibration procedures.

BRIEF DESCRIPTION OF THE INVENTION

In accordance with various embodiments, a nuclear medicine (NM) calibration source is provided. The NM calibration source includes an isotope source having an energy spectrum with at least one energy peak and a fluorescence layer adjacent the isotope source creating at least one additional energy peak in the energy spectrum.

In accordance with other embodiments, a nuclear medicine (NM) calibration source is provided. The NM calibration source includes a flood source comprising Cobalt 57 and a fluorescence layer on a back side of the flood source. The fluorescence layer comprises lead.

In accordance with yet other embodiments, a method for providing a nuclear medicine (NM) calibration source includes providing an isotope source having an energy spectrum with at least one energy peak. The method further includes attaching a fluorescence backing layer to the isotope source creating at least one additional energy peak in the energy spectrum.

In accordance with still other embodiments, a method for nuclear medicine (NM) system calibration is provided. The method includes providing an isotope source having an energy spectrum with at least one energy peak and attaching a multi-bore collimator to a nuclear camera. The collimator has a septa having x-ray fluorescence creating at least one additional energy peak in the energy spectrum in response to gamma radiation received from the isotope source. The method further includes using the least one energy peak and at least one additional energy peak for multi-energy calibration of the nuclear camera.

DETAILED DESCRIPTION OF THE INVENTION

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments provide systems and methods including a calibration source for a nuclear medicine (NM) imaging systems that enables calibration of detectors of the NM imaging systems at multiple energy peaks (e.g., two-peak energy calibration) using a single isotope. For example, in accordance with various embodiments, a flood source is provided that includes a fluorescence layer, which may be a back plate on the flood source, enabling the multi-peak energy calibration.

Full energy calibration with a standard flood source may be performed by practicing the methods and systems described herein. The calibration may be performed during imaging system manufacturing or in the field after installation with collimators attached to the detectors of the imaging system. Accordingly, a single acquisition may be performed with multiple peaks for calibration of the detectors. Additionally, increased radiation handling safety is provided.

Figure 1:
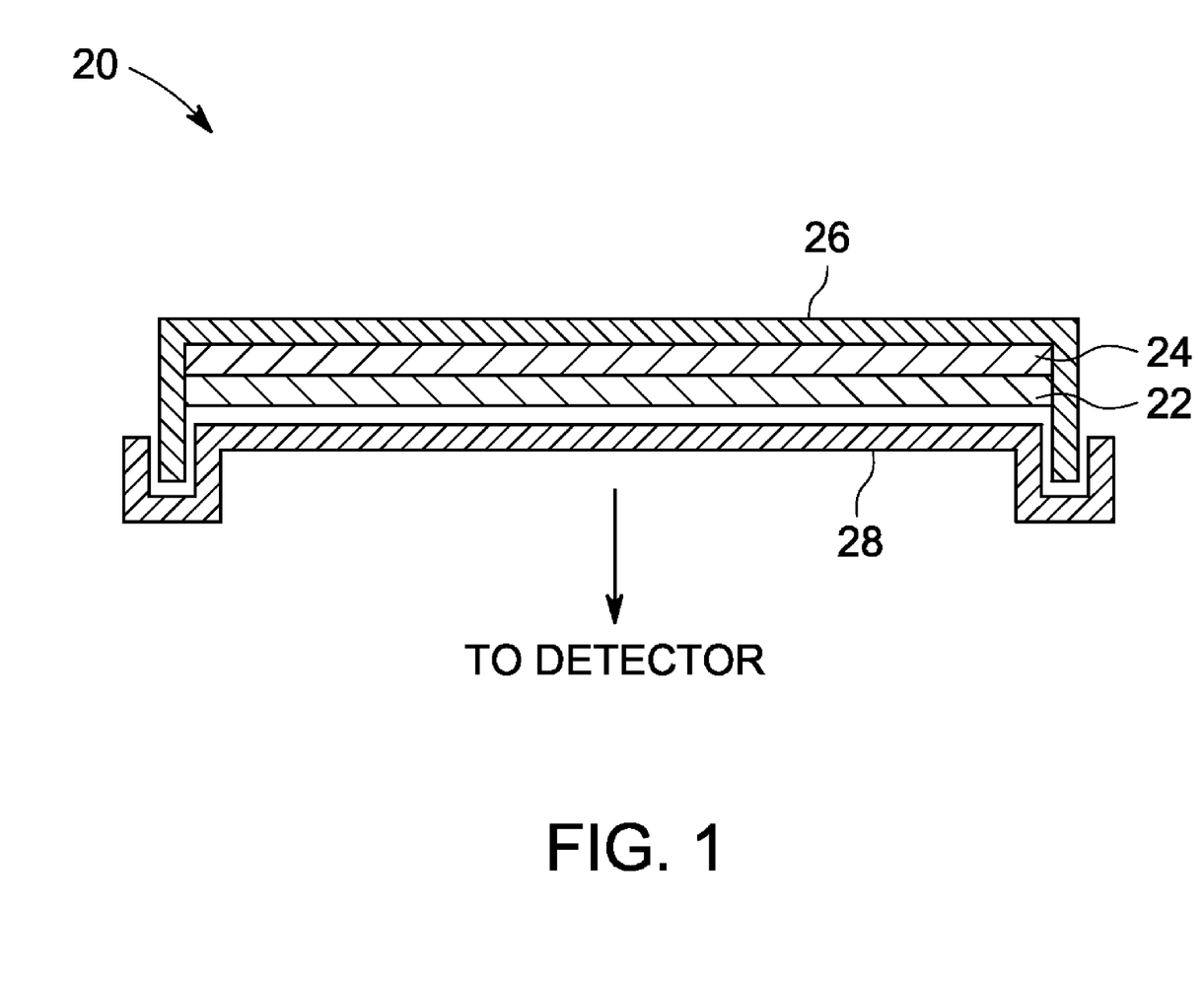
FIG. 1 is a cross-sectional view of a calibration source assembly formed in accordance with various embodiments.

Specifically, as shown in FIG. 1, a calibration source, illustrated as a calibration source assembly 20 is provided that enables multi-peak (e.g., a two peak) energy calibration using a single (common) isotope for calibration at all energy peaks. It should be noted that the term energy peak as used herein generally refers to the main energy emission from the decay of a radiopharmaceutical injected within a patient and which is calibrated by a corresponding isotope using the calibration source assembly 20. Additionally, the term energy window as used herein generally refers to the energy used for image reconstruction, which includes the photons with measured energy that fall within the energy range (defined by a width of an energy window) around the energy of the spectrum peak, which corresponds to the energy of the radioisotope as measured by a gamma camera or detector.

The calibration source assembly 20 generally includes an isotope source 22 having a fluorescence layer 24 illustrated as a back-side layer adjacent or coupled to a back side of the isotope source 22. The fluorescence layer 24 may be configured as a back plate or layer in some embodiments. For example, the isotope source 22 may be a generally planar radioactive flood source with an x-ray fluorescence backing layer defined by the fluorescence layer 24 on a back side thereof, for example, attached thereto. In some embodiments, the fluorescence layer 24 is a thin layer (e.g., 0.1-3.0 millimeters) on one side of the isotope source 22, such as supported thereon or coupled thereto (e.g., adhered with glue or another epoxy or coated thereon). The isotope source 22 having the fluorescence layer 24 generally forms the components used for calibrating an NM imaging system as described in more detail herein.

The calibration source assembly 20 may include optional components, particularly for supporting and/or storing the calibration source assembly 20. For example, a back cover 26 may be attached to the isotope source 22 and/or the fluorescence layer 24. In some embodiments, the back cover 26 is permanently attached to a back side of the isotope source 22 using a suitable coupling mechanism (e.g., a bracket or adhesive) such that the fluorescence layer 24 is between the back cover 26 and the isotope source 22. In other embodiments, the back cover 26 is removably attached to the isotope source 22 and/or fluorescence layer 24. The back cover 26 may be sized and shaped to fit within a storage container (not shown), for example, a radioactively shielded storage container for storing the isotope source 22 and the fluorescence layer 24 when not in use. The back cover 26 optionally may form part of the storage container. In various embodiments, the back cover 26 is made of lead and is used as the fluorescence layer 24 and as the back part of a shielding and storing case for storing the source 22 when not in use. Alternatively, a fluorescence layer 24 made of florescence\material is used, and the back cover 26 is made of radiation absorbing material such as tungsten. In this case, the back cover 26 is made thick enough to absorb substantially all the radiation emitted from the source 22. A hard lead alloy may be used to provide mechanical rigidity to the back cover 26, or an additional frame (not shown) may be added. In other embodiments, the isotope source preparation itself may provide the rigidity and to which the fluorescence layer 24 is adhered. Alternatively, Tungsten may be used as the fluorescence layer 24. Alternatively, the function of fluorescence and rigidity is combined by using Tungsten or another suitable material.

Additionally, a removable cover 28 (e.g., a removable front cover) may be provided that together with the back cover 26, which may be removably attached thereto, covers the isotope source 22 and the fluorescence layer 24. Accordingly, when the isotope source 22 and the fluorescence layer 24 are to be used for calibration, the removable cover 28 is removed exposing the isotope source 22 to one or more detector elements or modules of an NM imaging system as illustrated by the arrow in FIG. 1. In some embodiments, the removable cover 28 is used as the front part of a shielding and storing case for storing the source 22 when not in use. In this case, the removable cover 28 is made thick enough to absorb substantially all or much of the radiation emitted from the source 22. A hard lead alloy may be used to provide mechanical rigidity to the removable cover 28, or an additional frame (not shown) may be added. Alternatively, the removable cover 28 may be made of radiation absorbing material such as tungsten.

Figure 2:
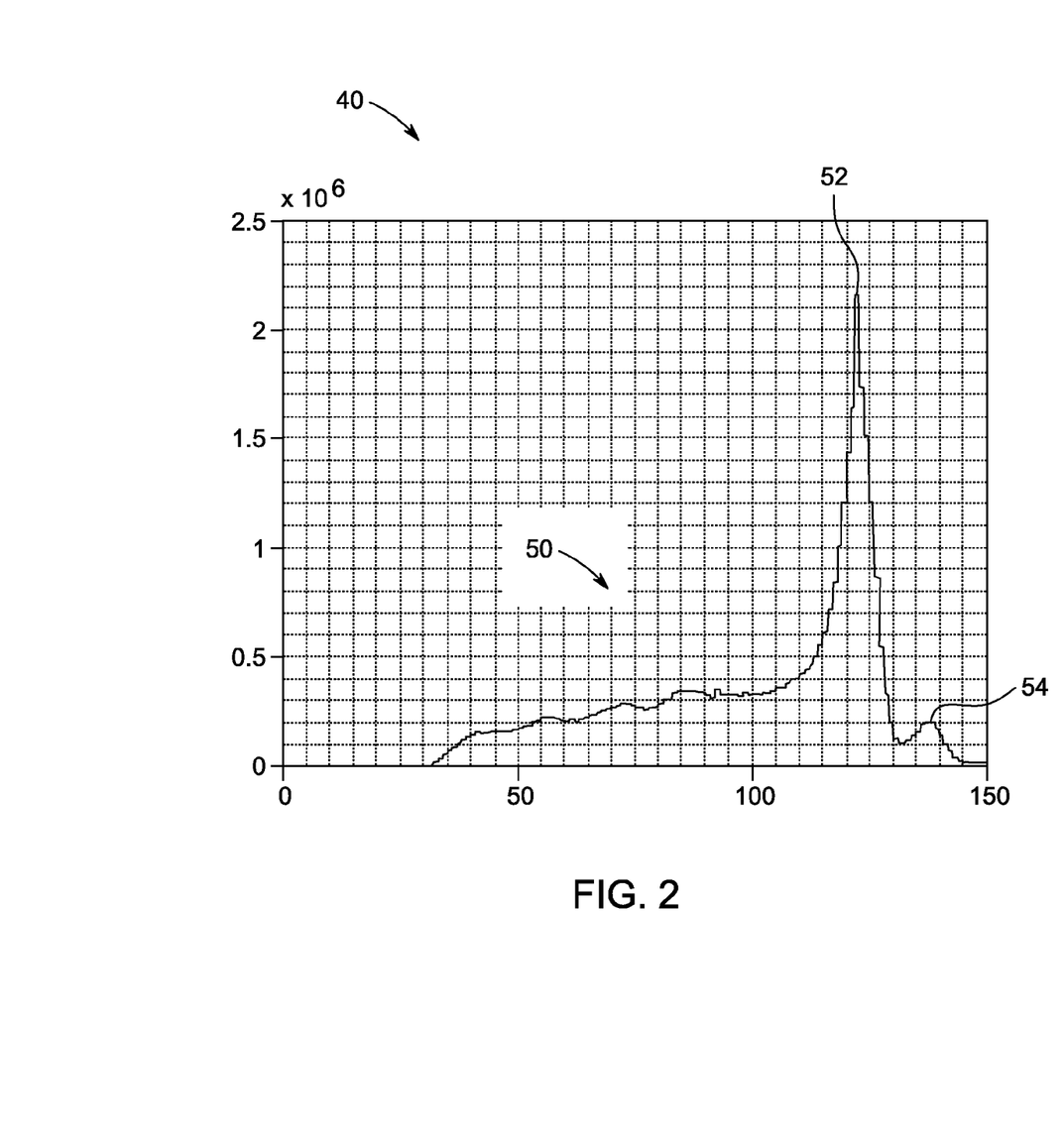
FIG. 2 is a graph illustrating an energy spectrum of Cobalt 57 from a flood source.

The isotope source 22 and the fluorescence layer 24 may be formed from different isotopes and materials, respectively. For example, in some embodiments, the isotope source 22 is formed from a Cobalt isotope with the fluorescence layer 24 formed from lead (Pb). The Cobalt isotope may be Cobalt 57 ($^{57}$Cobalt or Co57), which has an energy spectrum with an energy peak at about 122 keV as illustrated in graphs 40 and 42, respectively, of FIGS. 2 and 3. The horizontal axis of the graphs 40 and 42 represents energy and the vertical axis of the graphs 40 and 42 represents photon counts. In particular, the energy curve 50 shown in FIG. 2 corresponds to the energy spectrum of an isotope source 22 formed from Co57 showing an energy peak 52 at about 122 keV. A smaller energy peak 54 (i.e., an energy peak with a higher peak energy, but fewer counts) is also present at about 136.5 keV.

Figure 3:
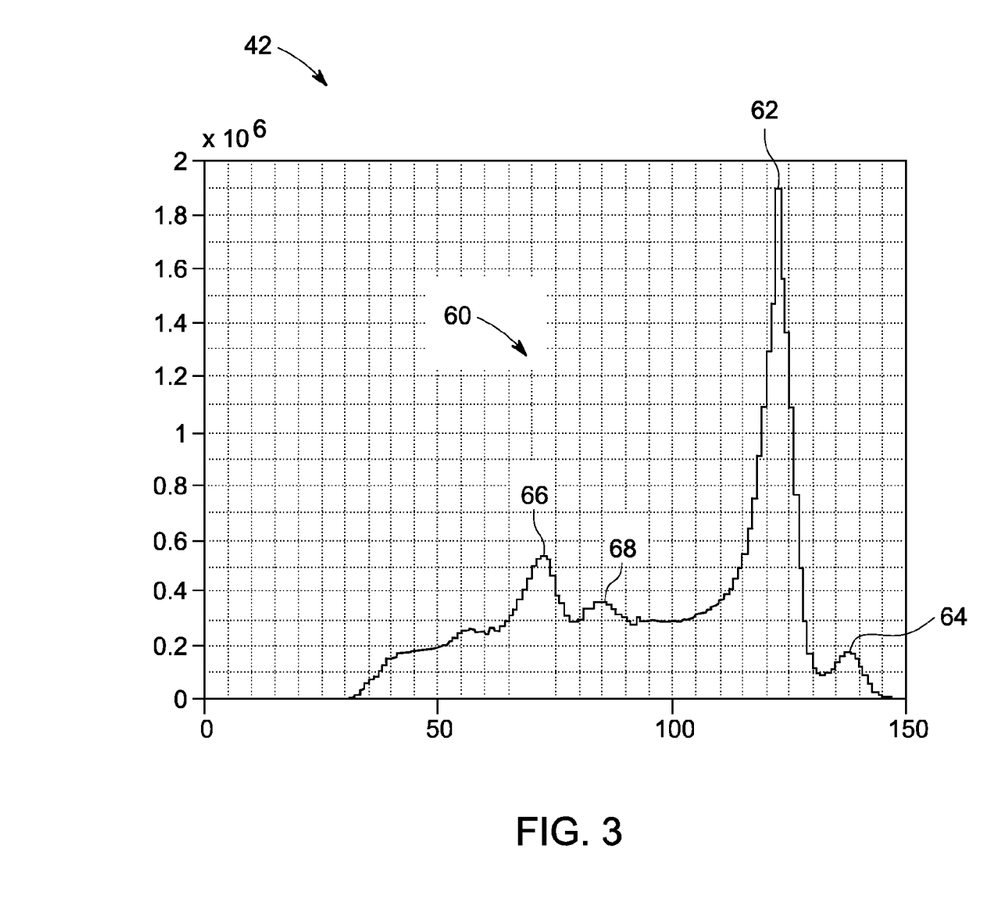
FIG. 3 is a graph illustrating an energy spectrum of Cobalt 57 from an isotope source having a fluorescence layer formed in accordance with various embodiments.

Similar energy peaks 62 and 64, corresponding to the energy peaks 52 and 54 respectively, are present in the energy curve 60 corresponding to the energy spectrum of an isotope source 22 formed from Co57 and also having the fluorescence layer 24 formed from Pb. Additionally, as a result of the fluorescence from the Pb in the fluorescence layer 24, different energy peaks are also formed at different energy levels as illustrated in FIG. 3. The Pb in the fluorescence layer 24 reradiates the gamma rays absorbed by the fluorescence layer 24, resulting in fluorescence at the different energy levels. In particular, as shown in FIG. 3, the energy curve 60 corresponding to the energy spectrum of the isotope source 22 formed from Co57 and also having the fluorescence layer 24 formed from Pb, further includes energy peaks 66 and 68 at about 75 keV and 85 keV. The energy peaks 66 and 68 correspond to the Pb fluorescence, namely a 75 keV Kα and 85 keV Kβ fluorescence from the Pb. It should be noted that when reference is made herein to a specific energy peak, the energy peak may also occur within an energy deviation from the described energy level, such as above or below the described energy level.

Thus, the isotope source 22 with the fluorescence layer 24 (e.g., a thin layer of Pb, such as a few millimeters (1-3 mm) on a Co57 flood source) places an identifiable 75 keV energy peak (and another 85 keV energy peak) in the energy spectrum that includes the 122 keV energy peak (and the 136.5 keV energy peak) from the Co57. Accordingly, gamma cameras or detectors may be calibrated, for example, calibrating a gain and offset using a plurality of energy peaks generated from a single isotope. In particular, with the isotope source 22 formed from Co57 and also having the fluorescence layer 24 formed from Pb, the Co57 provides the 122 keV and 136.5 keV energy peaks and the Pb adds the 75 keV energy peak (and also a lesser 85 keV energy peak). Accordingly, two or more of the energy peaks from the energy curve 60 may be used to calculate the gain and offset for a gamma camera or detector of an NM imaging system from a single acquisition and using known techniques in the art. Thus, the gain and offset for each pixel may be calibrated and used to define an energy map.

In some embodiments, the 75 keV and/or 122 keV energy peaks are also or alternatively used during detector calibration. For example, different energy peaks or more energy peaks may be used, such as the 75 keV, 122 keV and 136.5 keV energy peaks, to determine the offset, gain and quadratic term for each of plurality of pixels of a pixelated gamma camera or detector to thereby generate a calibration map using known techniques in the art. The added calibration accuracy provided using three peaks may be used for calibration of gamma cameras or detectors for clinical measurements with isotopes such as 111-indium that emits gamma rays at 170 keV and 240 KeV. Additional energy peaks also may be used, such as the lesser amplitude 85 keV energy peak.

It should be noted that different isotopes and materials may be used to form the calibration source assembly 20. For example, the isotope source 22 may be configured as a plastic box flood source filed with Technetium-99m (technetium-99m) providing an energy peak at 140.5 keV instead of the 122 keV energy peak of Co57. Also, different Cobalt isotopes may be used, for example, Co60. Additionally, and, for example, the fluorescence layer 24 may be coated with other materials to provide additional or different energy peaks. Additionally, materials other than Pb may be used to form the fluorescence layer 24. For example, the fluorescence layer 24 may be formed from, but not limited to bismuth, tungsten, tantalum, barium and tin.

The fluorescence layer 24 also may be formed from a multi-layer structure, for example, formed from a bi-layer of tungsten and Pb. In this multi-layer structure, the fluorescence from the tungsten creates an energy peak at 69 keV and the fluorescence from the Pb creates energy peaks at 75 keV and 85 keV.

It should be noted that the fluorescence layer 24 formed from Pb provides radiation shielding for an operator. For example, using a 1 mm layer of Pb on the isotope source 22 can reduce the radiation intensity of 140 keV by about 9/10. Additionally, the Pb layer may provide mechanical support for the isotope source 22 and vice versa.

Other modifications include, an optional thin layer (e.g., a thin 0.01-1.0 millimeter foil layer) provided on a front side of the isotope source 22 opposite the fluorescence layer 24. The front layer may be configured to enhance the peak ratio of the energy spectrum and may be formed from different materials, such as copper and brass. The front layer also may be configured to provide additional energy peaks and/or reduce the main intensity energy peak. Additionally, the thin layer may be configured such that all of the energy peaks are at about the same height or amplitude.

The calibration source assembly 20, including in particular, the isotope source 22 with the fluorescence layer 24 may be used to calibrate different types of NM imaging systems, such as NM imaging systems with collimated detectors, for example, multi-bore collimators or pinhole collimators. In operation, the isotope source 22 with the fluorescence layer 24 are used to calibrate the detectors by providing a known radioactive emission source (such as with a flood source) that defines an expected output from the detectors. Thereafter, the actual outputs from the detector elements, for example, outputs from the pixels of a pixelated detector may be used to calibrate the pixelated detector based on the difference between the expected output and the actual output. The calibration may be performed using any suitable method, for example, as known in the art.

Figure 4:
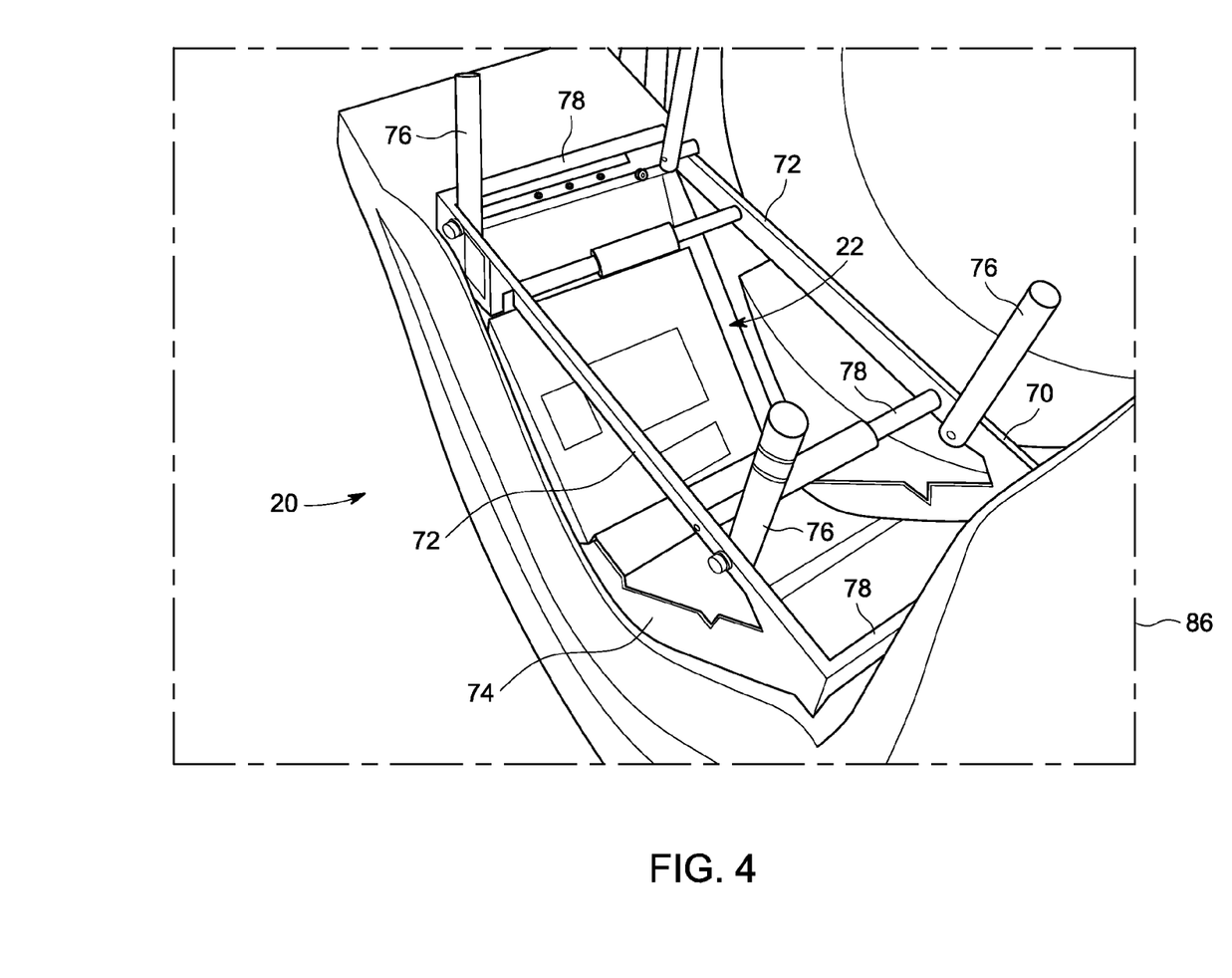
FIG. 4 is a perspective view of calibration source assembly formed in accordance with various embodiments supported within a nuclear medicine (NM) imaging system and having a fluorescence layer removed.
Figure 5:
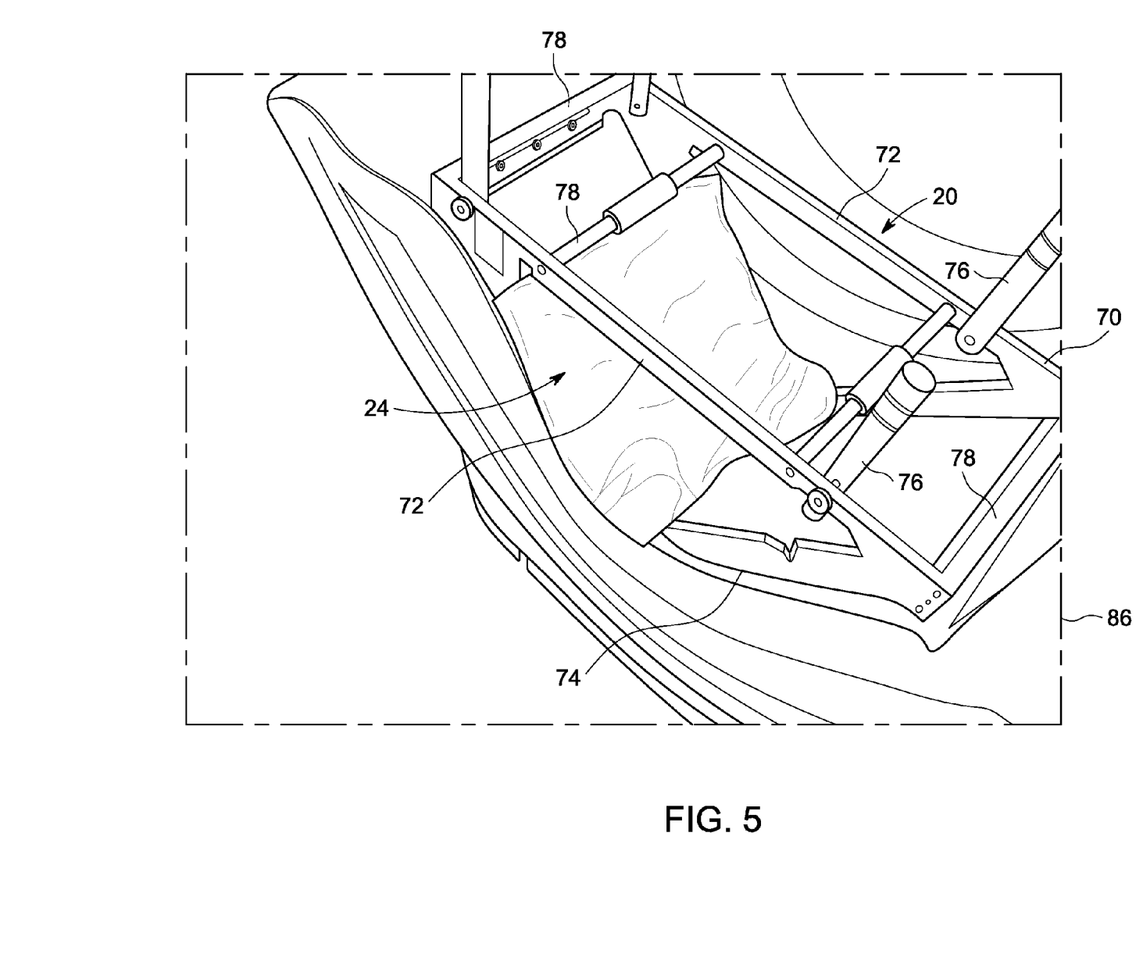
FIG. 5 is a perspective view of a calibration source assembly formed in accordance with various embodiments supported within an NM imaging system.
Figure 6:
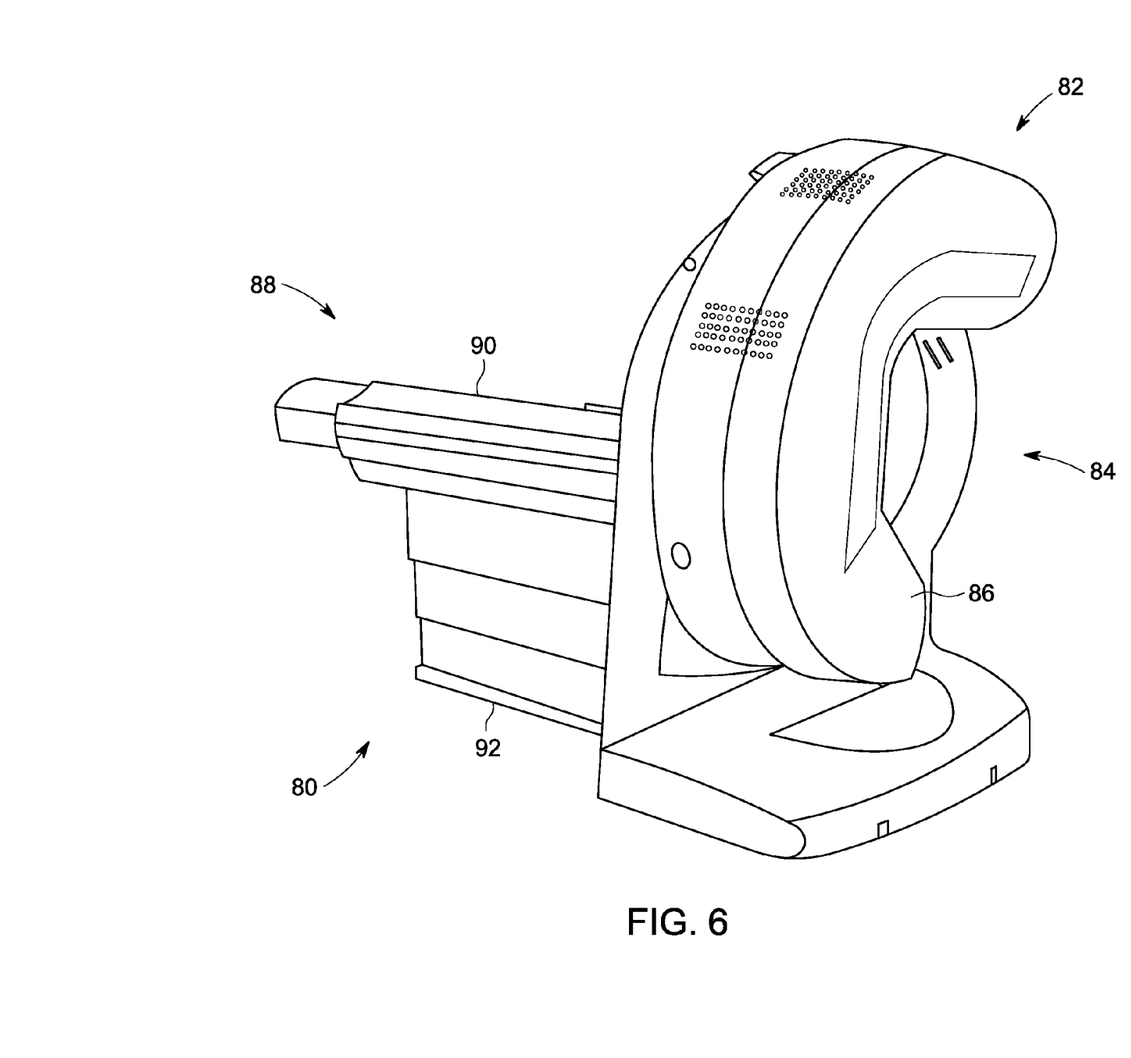
FIG. 6 is a perspective view of an NM imaging system in which various embodiments of a calibration source assembly may be implemented.
Figure 7:
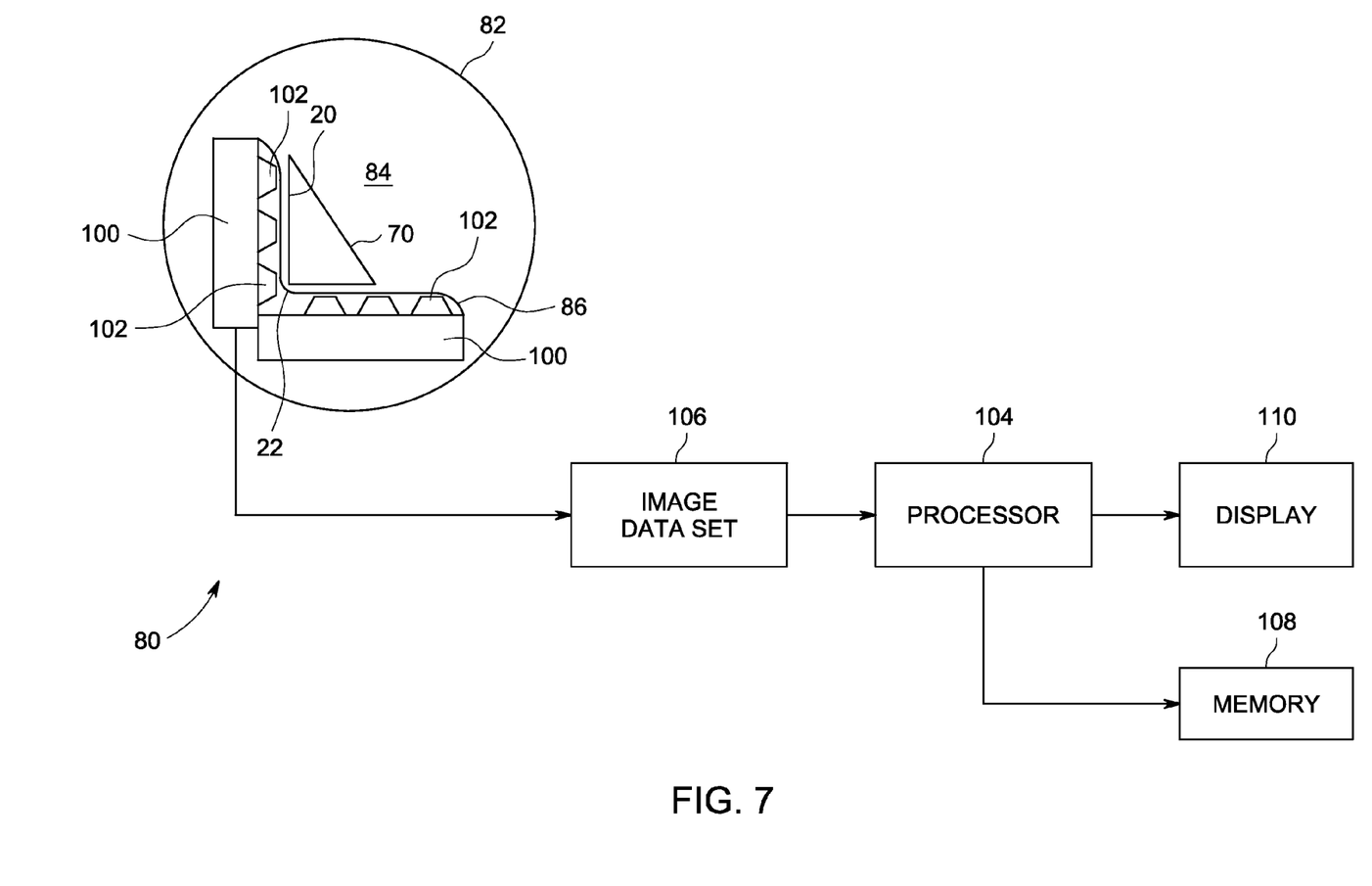
FIG. 7 is a block diagram illustrating an embodiment of the NM imaging system of FIG. 6 in which various embodiments of a calibration source assembly may be implemented.

The calibration source assembly 20 may be configured as shown in FIGS. 4 and 5 for calibration of an NM imaging system 80 as shown in FIGS. 6 and 7. Specifically, as shown in FIGS. 4 and 5, the calibration source assembly 20 may include a support member 70, illustrated as a frame and generally defining a jig for holding the calibration source assembly 20 within a gantry 82 inside a bore 84 of the NM imaging system 80 (shown in FIGS. 6 and 7), and more particularly, supported against a detector assembly 86. It should be noted that the calibration source assembly 20 is shown in FIG. 4 with the fluorescence layer 24 removed. The support member 70 is sized and shaped to fit within the gantry 82 inside the bore 84 and to encompass at least a portion of an inner circumference of the housing of the detector assembly 86, such as one-quarter, one-third, one-half, etc. of the detector assembly 86. Accordingly, in an exemplary embodiment, wherein the support member 70 is sized and shaped to fit within the gantry 82 inside the bore 84 and to encompass at least one-third of the detector assembly 86, one-third of the detector assembly is calibrated at one time with the support member 70 moved to calibrate the other portions of the detector assembly 86.

The support member 70 includes legs 72 that extend across the diameter of the detector assembly 86 and legs 74 that extend along the circumference of the detector assembly 86. One or more arms 76 also extend from the legs 72, for example, four arms 76 extend from end portions of the legs 72 to facilitate placement of the calibration source assembly 20 within the detector assembly 86 and removal therefrom. Cross-members 78 also may be provided, for example, transverse to the legs 72 and aligned axially along the housing of the detector assembly 86 to further support the calibration source assembly 20.

The NM imaging system 80 may be an NM diagnostic imaging system having collimated pixelated detectors, such as CZT detectors to detect event counts (e.g., SPECT photon counts). For example, as shown in FIG. 6, the NM imaging system 80 may be a diagnostic NM imaging system 80, which is shown embodied as a SPECT imaging system, such as the Discovery NM 530c imaging system available from GE Healthcare. The system 80 includes the gantry 82 (which may be an integrated gantry) having the bore 84 therethrough. The gantry 82 is configured to support one or more NM radiation detectors forming part of the detector assembly 86. The radiation detectors may be configured as CZT imaging modules, for example, CZT solid state detectors having focused collimation provided by a plurality of collimators. It should be noted that the NM radiation detectors may be supported around more or less of the gantry 82, for example, around the entire 360 degrees of the gantry 82 or a portion thereof, such as 180 degrees of the gantry 82. Thus, the radiation detectors are arranged around the bore 84 defining an examination axis.

A patient table 88 may be provided and include a bed 90 slidingly coupled to a bed support system 92, which may be coupled directly to a floor or may be coupled to the gantry 82 through a base coupled to the gantry 82. The bed 90 may include a stretcher slidingly coupled to an upper surface of the bed 90. The patient table 88 is configured to facilitate ingress and egress of a patient (not shown) into an examination position that is substantially aligned with the examination axis of the bore 84. During an imaging scan, the patient table 88 may be controlled to move the bed 90 and/or stretcher axially into and out of (as well as upward and downward within) the bore 84 to obtain event count information for the patient or a region of the patient. The operation and control of the imaging system 80 may be performed in any manner known in the art. It should be noted that the various embodiments may be implemented in connection with imaging systems that include stationary gantries or moving gantries.

The calibration source assembly 20 (shown in FIG. 1) may be supported within the detector assembly 86 as described and illustrated in more detail herein. A scanning operation is then performed to acquire event count information from the isotope source 22 with the fluorescence layer 24 (both shown in FIG. 1), which is detected by each of a plurality of pixels of the detectors of the detector assembly 86. Thereafter, calibration is performed as described in more detail herein.

Thus, as shown in FIG. 7, the NM imaging system 80 may include one or more detectors, such as a pair of detectors 100 (e.g., gamma detectors or gamma cameras) within the detector assembly 86 (such as housing thereof) and having the bore 84 therethrough. The bore 84 is configured to receive an object therein, such as a patient supported on a patient table 88 (shown in FIG. 6) or the calibration source assembly 20 or a portion thereof. The detectors 100 are shown in an "L" mode configuration, but may be moved and positioned in other configurations such as an "H" mode configuration. Additionally, the gantry 82 may be configured in different shapes, for example, as a "C", "H" or "L". It should be noted that more or less detectors 100 may be provided.

The detectors 100 are supported on the gantry 82 to acquire NM data, such as emission photon data. The detectors 100 may be formed from different materials, such as cadmium zinc telluride (CdZnTe), often referred to as CZT, cadmium telluride (CdTe), and silicon (Si), among others, or from Sodium Iodide (NaI) and used in combination with photomultiplier (PMT) tubes (not shown) as is known. In some embodiments, the detectors may be formed from a plurality of detector modules, each having a plurality of pixels.

One or more collimators 102 may be provided in combination with the detectors 100 (or modules thereof), for example, to provide focused collimation toward a region of interest (ROI). Thus, the actual field of view (FOV) for each of the detectors 100 (or portions thereof) may be decreased by the type of collimator, such as pinhole (or multi-pinhole) or converging collimator. Additionally, the actual FOV may be increased or remain relatively unchanged depending on the type of collimator 102 used. Additional examples of types of collimators 102 include parallel-beam converging, diverging fan-beam, converging or diverging cone-beam, multi-bore, multi-bore converging, multi-bore converging fan-beam, multi-bore converging cone-beam, multi-bore diverging, or other types of collimators.

The NM imaging system 80 also includes a processor 104 (e.g., workstation) that is coupled to the imaging system 80. During operation, the output from the detectors 100, which may be one or more image data sets 106 (or other image information), is transmitted to the processor 104 for processing, such as image reconstruction to form an image for display on a display 110 or for detector calibration.

Thus, for example, event count information, such as photon count information from the emissions of the isotope source 22 of the calibration source assembly 20 supported within the detector assembly 86 by the support member 70 is obtained from the detectors 100. It should be noted that the raw data, such as the image data sets 106, may be stored for a short term (e.g., during processing) or for a long term (e.g., for later offline retrieval) in a memory 108. The memory 108 may be any type of data storage device, which may also store databases or maps of information. The memory 108 may be separate from or form part of the processor 104.

The support member 70 is positioned such that calibration source assembly 20 is positioned in front of a portion of the detector assembly 86, such as positioning the planar surface of the calibration source assembly 20 in front of all off the collimators 102 (e.g., exposing all of pinholes to radiation) on one side (illustrated on the left side (vertical wall) in FIG. 7) of the detector assembly 86. The support member 70 is then moved to expose the collimators 102 on the lower portion of the detector assembly 86 (e.g., bottom side (horizontal wall) as illustrated in FIG. 7).

In some embodiments the nuclear camera is fitted with a multi-bore collimator substantially made of lead. The multi-bore collimator may be of a parallel-bore, fan-beam or cone-beam type as known in the art. In these embodiments, x-ray fluorescence is created when gamma radiation strike the collimator septa. X-ray fluorescence thus produced may be used, together with the main gamma energy peak, for dual or multi-peak calibration.

Thus, using the calibration source assembly of the various embodiments supported within an NM imaging system, multi-peak calibration of the NM imaging may be performed using a single isotope flood source. The calibration source assembly may be used to calibrate NM imaging systems having collimated detectors assembled thereto.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for nuclear medicine (NM) system calibration, the method comprising:
   providing an isotope source having an energy spectrum with at least one energy peak;
   attaching a multi-bore collimator to a nuclear camera, the collimator having septa having x-ray fluorescence creating at least one additional energy peak in the energy spectrum in response to gamma radiation received from the isotope source; and
   using the least one energy peak and at least one additional energy peak to generate a calibration map for multi-energy calibration of the nuclear camera to calibrate at least one of a gain or offset.

2. The method of claim 1, wherein using at least one energy peak comprises using a main gamma energy peak produced by the isotope source and another gamma energy peak produced by the x-ray fluorescence.

3. The method of claim 1, wherein the isotope source comprises a Cobalt 57 flood source.

4. The method of claim 1, wherein the isotope source comprises Technetium-99m in a box flood source.

5. The method of claim 1, wherein the nuclear camera is a gamma camera.

6. The method of claim 1, wherein the isotope source has an energy spectrum with at least two energy peaks.

7. The method of claim 1, wherein the multi-bore collimator comprises lead.

8. The method of claim 1, wherein the multi-bore collimator is one of a parallel-bore collimator, a fan-beam collimator or a cone-beam collimator.

9. The method of claim 1, wherein the x-ray fluorescence creates at least two additional energy peaks in the energy spectrum.

10. A nuclear medicine (NM) calibration source comprising:
    an isotope source having an energy spectrum with at least one energy peak; and
    a fluorescence layer adjacent the isotope source creating at least one additional energy peak in the energy spectrum, the fluorescence layer comprising a multi-layer structure formed from different materials, wherein the multi-layer structure comprises at least two layers and the at least two layers are on a same side of the isotope source.

11. The NM calibration source of claim 10, wherein the multi-layer structure comprises a bi-layer of tungsten and lead.

12. The NM calibration source of claim 11, wherein at one of the layers is formed from lead and configured to provide mechanical support of the isotope source.

13. The NM calibration source of claim 10, further comprising a front layer on a front side of the isotope source opposite the fluorescence layer and configured to enhance a peak ratio of the energy spectrum.

14. The NM calibration source of claim 10, further comprising a front layer on a front side of the isotope source opposite the fluorescence layer and configured to reduce a main energy peak of the energy spectrum.

15. The NM calibration source of claim 10, further comprising a front layer on a front side of the isotope source opposite the fluorescence layer and configured to provide a plurality of energy peaks at about a same amplitude.

16. The NM calibration source of claim 10, further comprising a removable front cover forming a front part of a shield and storing case, the removable front cover formed from a hard lead alloy.

17. The NM calibration source of claim 10, wherein the multi-layer structure is positioned as a backing for the isotope source.

18. The NM calibration source of claim 10, wherein the multi-layer structure is positioned between the isotope source and a gamma camera.

19. The NM calibration source of claim 10, wherein the isotope source comprises a Cobalt 57 flood source.

20. The NM calibration source of claim 10, wherein the fluorescence layer comprises lead.

21. The NM calibration source of claim 10, further comprising a backing layer having a thickness to absorb substantially all radiation emitted from the isotope source and a removable cover forming a container configured to shield and store the isotope source.

22. The NM calibration source of claim 10, wherein the isotope source comprises Technetium-99m in a box flood source.

23. The NM calibration source of claim 10, wherein the isotope source has an energy spectrum with at least two energy peaks.

24. The NM calibration source of claim 10, wherein the fluorescence layer creates at least two additional energy peaks in the energy spectrum.

25. The NM calibration source of claim 10, wherein the fluorescence layer comprises a coating providing at least one additional energy peak in the energy spectrum.

26. The NM calibration source of claim 10, further comprising a multi-pinhole collimator.

27. A nuclear medicine (NM) calibration source comprising:
   a flood source having an energy spectrum with at least one energy peak; and
   a fluorescence layer on a back side of the flood source creating at least one additional energy peak in the energy spectrum, the fluorescence layer comprising a multi-layer structure having at least two layers formed from different materials and the at least two layers on a same side of the flood source, wherein one of the materials is lead, and the fluorescence layer forming a back cover of a shielding and storing case for storing the flood source; and
   a removable cover forming a front part of the shielding and storing case configured to shield and store the flood source when not in use.

28. The NM calibration source of claim 27, wherein the removable cover is formed from a hard lead alloy and configured to provide mechanical rigidity to support the flood source.

29. The NM calibration source of claim 27, wherein the fluorescence layer comprises a lead layer having a thickness of about one millimeter.

30. The NM calibration source of claim 27, wherein the fluorescence layer further comprises tungsten.

31. The NM calibration source of claim 27, further comprising a metal foil on a front side of the flood source, the metal foil comprising one of copper or brass.

32. The NM calibration source of claim 27, further comprising a back cover attached to the fluorescence layer and the removable cover attached to the back cover.

33. A method for providing a nuclear medicine (NM) calibration source, the method comprising:
   providing an isotope source having an energy spectrum with at least one energy peak; and
   attaching a fluorescence backing layer to the isotope source creating at least one additional energy peak in the energy spectrum, the fluorescence backing layer forming a back cover of a shielding and storing case for storing the isotope source, the fluorescence backing layer comprising a multi-layer structure formed from different materials, wherein the multi-layer structure comprises at least two layers and the at least two layers are on a same side of the isotope source.

34. The method of claim 33, wherein the isotope source comprises a flood source and further comprising using the isotope source with the attached fluorescence layer to calibrate a collimated NM detector assembly of an NM imaging system.

* * * * *